US006812018B2

(12) United States Patent
Wicher et al.

(10) Patent No.: US 6,812,018 B2
(45) Date of Patent: Nov. 2, 2004

(54) THERMOSTABLE CELLULASE (75) Inventors: Krzysztof B. Wicher, Cracow (PL); Olof Peder Holst, Lund (SE); Maher Youssef Abou Hachem, Lund (SE); Eva Margareta Nordberg Karlsson, Lund (SE); Gudmundur O. Hreggvidsson, Reykjavik (IS)

(73) Assignee: Prokaria Ltd., Reykjavik (IS)

( * ) Notice: Subject to any disclaimer, the term of this patent is extended or adjusted under 35 U.S.C. 154(b) by 0 days.

(21) Appl. No.: 10/003,759

(22) Filed: Oct. 23, 2001

(65) Prior Publication Data

US 2002/0102699 A1 Aug. 1, 2002

Related U.S. Application Data (63) Continuation-in-part of application No. PCT/IS01/00012, filed on Jun. 15, 2001, which is a continuation-in-part of application No. 09/594,884, filed on Jun. 15, 2000, now abandoned.

(51) Int. Cl.$^7$ .............................. C07H 4/04; C12P 4/06; C12N 9/00; C12N 9/42; C12N 1/20
(52) U.S. Cl. ................................ 435/209; 435/4; 435/6; 435/41; 435/69.1; 435/183; 435/200; 435/252.3; 435/320.1; 530/350; 536/23.2; 536/23.4; 536/23.7
(58) Field of Search ............................... 435/4, 6, 69.1, 435/183, 200–209, 252.3, 320.1; 530/350; 536/23.2, 23.4, 23.7

(56) References Cited

U.S. PATENT DOCUMENTS

| | | | |
|---|---|---|---|
| 4,795,101 A | 1/1989 | Silver | 241/12 |
| 4,912,056 A | 3/1990 | Olson | 435/263 |
| 4,966,850 A | 10/1990 | Yu et al. | 435/200 |
| 5,445,957 A | 8/1995 | Rohde, Jr. et al. | 435/200 |
| 5,525,193 A | 6/1996 | Franks et al. | 162/5 |
| 5,677,151 A | 10/1997 | Wilson et al. | 435/72 |
| 5,700,686 A | 12/1997 | Foody et al. | 435/263 |
| 5,792,641 A | 8/1998 | Schülein et al. | 435/209 |
| 5,811,381 A | 9/1998 | Emalfarb et al. | 510/320 |
| 5,883,066 A | 3/1999 | Herbots et al. | 510/392 |
| 5,904,736 A | 5/1999 | Maurer et al. | 8/137 |
| 5,919,271 A | 7/1999 | Baillely et al. | 8/137 |
| 5,948,454 A | 9/1999 | Virkki et al. | 426/53 |
| 6,008,032 A | 12/1999 | Mathur et al. | 435/209 |
| 6,063,611 A | 5/2000 | Van Solingen | 435/209 |
| 6,066,233 A | 5/2000 | Olsen et al. | 162/5 |

FOREIGN PATENT DOCUMENTS

| | | |
|---|---|---|
| WO | WO 97/11165 | 3/1997 |
| WO | WO 97/33982 | 9/1997 |
| WO | WO 97/34005 | 9/1997 |
| WO | WO 97/44361 | 11/1997 |
| WO | WO 98/01569 | 1/1998 |
| WO | WO 98/12307 | 3/1998 |
| WO | WO 98/13465 | 4/1998 |
| WO | WO 98/33895 | 8/1998 |
| WO | WO 99/10481 | 3/1999 |
| WO | WO 99/31255 | 6/1999 |
| WO | WO 00/09707 | 2/2000 |
| WO | WO 00/14208 | 3/2000 |
| WO | WO 00/37614 | 6/2000 |

OTHER PUBLICATIONS

Ohmiya et al. (J. Bacteriol., 1991, vol. 173(2):636–641).*
Halldorsdottir et al. Appl. Microbiol. Biotechnol., 1998, vol. 49:277–284.*
Gilkes et al. Microbiol. Rev., 1991, vol. 55(2):303.*
Halldorsdottir et al.GenBank Accession No.RMU72637, May 11, 1999.*
Hreggvidsson, G. O. et al., "An Extremely Thermostable Cellulase from the Thermophilic Eubacterium *Rhodothermus marinus,*" *Applied and Environmental Microbiology*, 62 (8) :3047–3049 (1996).
Halldórsdóttir, S. et al., "Cloning, Sequencing and Overexpression of a *Rhodothermus marinus* Gene Encoding a Thermostable Cellulase of Glycosyl Hydrolase Family 12," *Appl. Microbiol. Biotechnol.*, 49:277–284 (1998).
Bauer, M.W. et al., "An Endoglucanase, EglA, from the Hyperthermophilic Archaeon *Pyrococcus furiosus* Hydrolyes β–1,4 Bonds in Mixed–Linkage (1→3), (1→4)–β–D–Glucans and Cellulose," *Journal of Bacteriology*, 181 (1): 284–290 (1999).
GenBank Accession No. U72637, "*Rhodothermus marinus* Cellulase (celA) Gene, Complete cds.," May 1999 [retrieved on May 31, 2000].
GenBank Accession No. AF181032, "*Pyrococcus furiosus* Endoglucanase A Precursor (eglA) Gene, Complete cds.", Nov. 1999 [retrieved on Jun. 12, 2000].
Henrissat, B., "A Classification of Glycosyl Hydrolases Based on Amino Acid Sequence Similarities," *J. Biochem.*, 280:309–316 (1991).
Henrissat, B. and Bairoch, A., "New Families in the Classification of Glycosyl Hydrolases Based on Amino Acid Sequence Similarities," *J. Biochem.*, 293:781–788 (1993).
Wicher, K.B., et al., "Deletion of a Cytotoxic, N–terminal Putative Signal Peptide Results in a Significant Increase in Production Yields in *Escherichia coli* and Improved Specific Activity of Cell2A from *Rhodothermus marinus,*" *Appl. Microbiol. Biotechnol.*, 55:578–584 (2001).

* cited by examiner

*Primary Examiner*—Manjunath Rao
(74) *Attorney, Agent, or Firm*—Hamilton, Brook, Smith & Reynolds, P.C.

(57) ABSTRACT

Disclosed are variant thermostable cellulases, nucleic acids encoding the variants and methods for producing the variants. The variant thermostable cellulases have the amino acid sequence of a glycosyl hydrolase of family 12 wherein one or more amino acid residues which are not part of the catalytic domain are deleted. In specific embodiments, the variant thermostable cellulase is a variant of Cel12A of *Rhodothermus marinus.*

18 Claims, 2 Drawing Sheets

S. P. - signal peptide  [EP]₄ - linker  C. D. - catalytic domain
H.t. - HSV tag from pET25b(+)  H₆ - hexa histidine tag

SEQUENCE LISTING

<160> NUMBER OF SEQ ID NOS: 10

<210> SEQ ID NO 1
<211> LENGTH: 1877
<212> TYPE: DNA
<213> ORGANISM: Rhodothermus marinus
<220> FEATURE:
<221> NAME/KEY: CDS
<222> LOCATION: (710)..(1495)
<223> OTHER INFORMATION:

<400> SEQUENCE: 1

| | | | | | | |
|---|---|---|---|---|---|---|
| gggcgagtcg | aacgtcgggc | gcgcctcgca | gatcgaacgg | ctcttcccac | gctgattcgc | 60 |
| tgcgtgcgca | cgcactgggc | gctgggcgag | tttcccttct | acttcgtcca | gattgcccct | 120 |
| tacgactacg | ggccgaacgc | ccgcacgcag | cgtgtccggg | aagcgcagtt | gcgcaccatg | 180 |
| tgcgcgtgcc | tcatacgggt | atggtcgtga | ccaccgatgt | gggcgacgac | cacaacacta | 240 |
| cctccggcgc | gacaacgtga | agtggcgagc | gcctggcctc | tgggcgctgg | ccaacgacta | 300 |
| cggcttccgg | gatgtggtct | actccggtcc | catctacgaa | cgcatggaac | gtgaggatgg | 360 |
| ccgcctgcgg | ctctatttcc | gctatgccga | aggggggactg | gtcctgcgcc | cggccgacgg | 420 |
| cggcggcgag | ttcgtgattg | cgggaccgga | ccgtgtcttc | cacccggcgc | gggtacgggt | 480 |
| cgaaggcgaa | acgctggtgg | tgtggagtcc | gcgcgtctcc | gatccgcagg | cggtgcgcta | 540 |

-continued

```
tggctggtcc aatacgccgc acgccacgct gttcaaccgg gccggcctgc ccgcttcgcc      600
cttccgcacc gacgactggc cggaaggcga ctgagcgacg caaccggtgc ttgcatgcga      660
caggggcact tcgtaccttg aagtgccctt tgtcatttca atggaataa atg aac gtc     718
                                                     Met Asn Val
                                                       1 atg cgt gcg gta ctg gtc ctg agc ctg tta ttg ctg ttt gga tgc gac       766
Met Arg Ala Val Leu Val Leu Ser Leu Leu Leu Leu Phe Gly Cys Asp
  5              10                  15 tgg ctc ttt ccc gat ggc gac aac gga aag gaa ccg gag cct gag ccc       814
Trp Leu Phe Pro Asp Gly Asp Asn Gly Lys Glu Pro Glu Pro Glu Pro
 20              25                  30                  35 gag ccg acc gtc gag ctg tgc gga cgc tgg gac gcg cgc gat gtg gcc       862
Glu Pro Thr Val Glu Leu Cys Gly Arg Trp Asp Ala Arg Asp Val Ala
                     40                  45                  50 ggg ggg cgc tac cgg gtg atc aac aac gta tgg ggc gcg gag acc gcc       910
Gly Gly Arg Tyr Arg Val Ile Asn Asn Val Trp Gly Ala Glu Thr Ala
                 55                  60                  65 cag tgc att gag gtc gga ctg gaa acg ggc aac ttc acg atc aca cgg       958
Gln Cys Ile Glu Val Gly Leu Glu Thr Gly Asn Phe Thr Ile Thr Arg
         70                  75                  80 gcc gat cac gac aac ggc aac aac gtg gcc gcc tat ccg gcc atc tac      1006
Ala Asp His Asp Asn Gly Asn Asn Val Ala Ala Tyr Pro Ala Ile Tyr
     85                  90                  95 ttc ggg tgc cac tgg ggc gcc tgc acg agc aat tcg gga ttg ccg cgg      1054
Phe Gly Cys His Trp Gly Ala Cys Thr Ser Asn Ser Gly Leu Pro Arg
100                 105                 110                 115 cgc gtg cag gag ctg tcc gac gtg cgc acg agc tgg acg ctc acg ccg      1102
Arg Val Gln Glu Leu Ser Asp Val Arg Thr Ser Trp Thr Leu Thr Pro
                    120                 125                 130 atc acg acg ggc cgc tgg aat gcc gcc tac gac atc tgg ttc agt ccc      1150
Ile Thr Thr Gly Arg Trp Asn Ala Ala Tyr Asp Ile Trp Phe Ser Pro
                135                 140                 145 gtc acg aat tcc ggc aac ggc tac agc ggc ggc gcc gag ctg atg atc      1198
Val Thr Asn Ser Gly Asn Gly Tyr Ser Gly Gly Ala Glu Leu Met Ile
            150                 155                 160 tgg ctg aac tgg aac ggc ggc gtg atg ccg ggc ggc agc cgc gtg gcc      1246
Trp Leu Asn Trp Asn Gly Gly Val Met Pro Gly Gly Ser Arg Val Ala
165                 170                 175 acc gtg gaa ctg gcc ggg gcc acc tgg gaa gtc tgg tat gcc gac tgg      1294
Thr Val Glu Leu Ala Gly Ala Thr Trp Glu Val Trp Tyr Ala Asp Trp
180                 185                 190                 195 gac tgg aat tac atc gcc tac cgg cgc acg acg ccc acc acg tcg gtg      1342
Asp Trp Asn Tyr Ile Ala Tyr Arg Arg Thr Thr Pro Thr Thr Ser Val
                    200                 205                 210 agc gag ctg gac ctg aag gcc ttc atc gac gac gcg gtc gcc cgc ggc      1390
Ser Glu Leu Asp Leu Lys Ala Phe Ile Asp Asp Ala Val Ala Arg Gly
                215                 220                 225 tac atc cgg ccg gag tgg tat ctg cat gcg gtg gag acg ggc ttc gaa      1438
Tyr Ile Arg Pro Glu Trp Tyr Leu His Ala Val Glu Thr Gly Phe Glu
            230                 235                 240 ctc tgg gag ggc ggg gcc ggt ctg cga agc gcc gat ttt tcc gta acg      1486
Leu Trp Glu Gly Gly Ala Gly Leu Arg Ser Ala Asp Phe Ser Val Thr
245                 250                 255 gtg cag tag cctgtcacac gggcaccagc gtaggccaga gaagcacccg              1535
Val Gln
260 tcggggcgct tatgcgggcg gccgtcgctt tgtgcctgac tttgtagtgc gctacggagg    1595 cgtcagccgg cgtggtgcgt ttccctggag gcgcttcgtt tcgtgccgga cgagaactta    1655
```

```
tccgaaaagc aagggagaga cctggtaagc cagggctttg cactgcgcac cagaagcacg   1715
ggtttgtagt aagccacgaa ggcgtccgcc gaagtggcct cacccgcgac ggcacttcgc   1775
tgcgctccgt gcctgactac gagcgcgttg ccgtgcttc aaacggcagg ctataaagct    1835
atacaggtcg aaatcgcgaa cttctccgac acttacaaac ac                     1877
```

<210> SEQ ID NO 2
<211> LENGTH: 261
<212> TYPE: PRT
<213> ORGANISM: Rhodothermus marinus

<400> SEQUENCE: 2

```
Met Asn Val Met Arg Ala Val Leu Val Leu Ser Leu Leu Leu Leu Phe
1               5                   10                  15

Gly Cys Asp Trp Leu Phe Pro Asp Gly Asp Asn Gly Lys Glu Pro Glu
            20                  25                  30

Pro Glu Pro Glu Pro Thr Val Glu Leu Cys Gly Arg Trp Asp Ala Arg
        35                  40                  45

Asp Val Ala Gly Gly Arg Tyr Arg Val Ile Asn Asn Val Trp Gly Ala
    50                  55                  60

Glu Thr Ala Gln Cys Ile Glu Val Gly Leu Glu Thr Gly Asn Phe Thr
65                  70                  75                  80

Ile Thr Arg Ala Asp His Asp Asn Gly Asn Asn Val Ala Ala Tyr Pro
                85                  90                  95

Ala Ile Tyr Phe Gly Cys His Trp Gly Ala Cys Thr Ser Asn Ser Gly
            100                 105                 110

Leu Pro Arg Arg Val Gln Glu Leu Ser Asp Val Arg Thr Ser Trp Thr
        115                 120                 125

Leu Thr Pro Ile Thr Thr Gly Arg Trp Asn Ala Ala Tyr Asp Ile Trp
    130                 135                 140

Phe Ser Pro Val Thr Asn Ser Gly Asn Gly Tyr Ser Gly Gly Ala Glu
145                 150                 155                 160

Leu Met Ile Trp Leu Asn Trp Asn Gly Gly Val Met Pro Gly Gly Ser
                165                 170                 175

Arg Val Ala Thr Val Glu Leu Ala Gly Ala Thr Trp Glu Val Trp Tyr
            180                 185                 190

Ala Asp Trp Asp Trp Asn Tyr Ile Ala Tyr Arg Arg Thr Thr Pro Thr
        195                 200                 205

Thr Ser Val Ser Glu Leu Asp Leu Lys Ala Phe Ile Asp Asp Ala Val
    210                 215                 220

Ala Arg Gly Tyr Ile Arg Pro Glu Trp Tyr Leu His Ala Val Glu Thr
225                 230                 235                 240

Gly Phe Glu Leu Trp Glu Gly Gly Ala Gly Leu Arg Ser Ala Asp Phe
                245                 250                 255

Ser Val Thr Val Gln
            260
```

<210> SEQ ID NO 3
<211> LENGTH: 786
<212> TYPE: DNA
<213> ORGANISM: Rhodothermus marinus

<400> SEQUENCE: 3

```
atgaacgtca tgcgtgcggt actggtcctg agcctgttat tgctgtttgg atgcgactgg   60
ctctttcccg atggcgacaa cggaaaggaa ccggagcctg agcccgagcc gaccgtcgag   120
```

-continued

```
ctgtgcggac gctgggacgc gcgcgatgtg gccggggggc gctaccgggt gatcaacaac      180
gtatggggcg cggagaccgc ccagtgcatt gaggtcggac tggaaacggg caacttcacg      240
atcacacggg ccgatcacga caacggcaac aacgtggccg cctatccggc catctacttc      300
gggtgccact ggggcgcctg cacgagcaat tcggattgc cgcggcgcgt gcaggagctg       360
tccgacgtgc gcacgagctg gacgctcacg ccgatcacga cgggccgctg gaatgccgcc      420
tacgacatct ggttcagtcc cgtcacgaat tccggcaacg gctacagcgg cggcgccgag      480
ctgatgatct ggctgaactg gaacggcggc gtgatgccgg cggcagccg cgtggccacc       540 gtggaactgg ccggggccac ctgggaagtc tggtatgccg actgggactg gaattacatc      600
gcctaccggc gcacgacgcc caccacgtcg gtgagcgagc tggacctgaa ggccttcatc      660
gacgacgcgg tcgcccgcgg ctacatccgg ccggagtggt atctgcatgc ggtggagacg      720
ggcttcgaac tctgggaggg cggggccggt ctgcgaagcg ccgattttc cgtaacggtg       780 cagtag                                                                 786
```

<210> SEQ ID NO 4
<211> LENGTH: 1134
<212> TYPE: DNA
<213> ORGANISM: Pyrococcus furiosus
<220> FEATURE:
<221> NAME/KEY: exon
<222> LOCATION: (82)..(1041)
<223> OTHER INFORMATION:

<400> SEQUENCE: 4

```
gaatgtcggg gcagattacg aagagagaag agctcttttt tataccttat attcaaatct      60
aacaaatttg gaggatgtcc a atg agc aag aaa aag ttc gtc atc gta tct      111
                        Met Ser Lys Lys Lys Phe Val Ile Val Ser
                         1               5                  10 atc tta aca atc ctt tta gta cag gca ata tat ttt gta gaa aag tat      159
Ile Leu Thr Ile Leu Leu Val Gln Ala Ile Tyr Phe Val Glu Lys Tyr
             15                  20                  25 cat acc tct gag gac aag tca act tca aat acc tca tct aca cca ccc      207
His Thr Ser Glu Asp Lys Ser Thr Ser Asn Thr Ser Ser Thr Pro Pro
         30                  35                  40 caa aca aca ctt tcc act acc aag gtt ctc aag att aga tac cct gat      255
Gln Thr Thr Leu Ser Thr Thr Lys Val Leu Lys Ile Arg Tyr Pro Asp
     45                  50                  55 gac ggt gag tgg cca gga gct cct att gat aag gat ggt gat ggg aac      303
Asp Gly Glu Trp Pro Gly Ala Pro Ile Asp Lys Asp Gly Asp Gly Asn
 60                  65                  70 cca gaa ttc tac att gaa ata aac cta tgg aac att ctt aat gct act      351
Pro Glu Phe Tyr Ile Glu Ile Asn Leu Trp Asn Ile Leu Asn Ala Thr
75                  80                  85                  90 gga ttt gct gag atg acg tac aat tta acc agc ggc gtc ctt cac tac      399
Gly Phe Ala Glu Met Thr Tyr Asn Leu Thr Ser Gly Val Leu His Tyr
                 95                 100                 105 gtc caa caa ctt gac aac att gtc ttg agg gat aga agt aat tgg gtg      447
Val Gln Gln Leu Asp Asn Ile Val Leu Arg Asp Arg Ser Asn Trp Val
            110                 115                 120 cat gga tac ccc gaa ata ttc tat gga aac aag cca tgg aat gca aac      495
His Gly Tyr Pro Glu Ile Phe Tyr Gly Asn Lys Pro Trp Asn Ala Asn
        125                 130                 135 tac gca act gat ggc cca ata cca tta ccc agt aaa gtt tca aac cta      543
Tyr Ala Thr Asp Gly Pro Ile Pro Leu Pro Ser Lys Val Ser Asn Leu
    140                 145                 150
```

-continued

| | | |
|---|---|---|
| aca gac ttc tat cta aca atc tcc tat aaa ctt gag ccc aag aac gga<br>Thr Asp Phe Tyr Leu Thr Ile Ser Tyr Lys Leu Glu Pro Lys Asn Gly<br>155                                160                                165                             170 | 591 |
| ctg cca att aac ttc gca ata gaa tcc tgg tta acg aga gaa gct tgg<br>Leu Pro Ile Asn Phe Ala Ile Glu Ser Trp Leu Thr Arg Glu Ala Trp<br>                          175                                180                                185 | 639 |
| aga aca aca gga att aac agc gat gag caa gaa gta atg ata tgg att<br>Arg Thr Thr Gly Ile Asn Ser Asp Glu Gln Glu Val Met Ile Trp Ile<br>                        190                                195                                200 | 687 |
| tac tat gac gga tta caa ccg gct ggc tcc aaa gtt aag gag att gta<br>Tyr Tyr Asp Gly Leu Gln Pro Ala Gly Ser Lys Val Lys Glu Ile Val<br>                       205                                210                               215 | 735 |
| gtc cca ata ata gtt aac gga aca cca gta aat gct aca ttt gaa gta<br>Val Pro Ile Ile Val Asn Gly Thr Pro Val Asn Ala Thr Phe Glu Val<br>                       220                                225                               230 | 783 |
| tgg aag gca aac att ggt tgg gag tat gtt gca ttt aga ata aag acc<br>Trp Lys Ala Asn Ile Gly Trp Glu Tyr Val Ala Phe Arg Ile Lys Thr<br>235                                240                                245                             250 | 831 |
| cca atc aaa gag gga aca gtg aca att cca tac gga gca ttt ata agt<br>Pro Ile Lys Glu Gly Thr Val Thr Ile Pro Tyr Gly Ala Phe Ile Ser<br>                          255                                260                               265 | 879 |
| gtt gca gcc aac att tca agc tta cca aat tac aca gaa ctt tac tta<br>Val Ala Ala Asn Ile Ser Ser Leu Pro Asn Tyr Thr Glu Leu Tyr Leu<br>                       270                                275                               280 | 927 |
| gag gac gtg gag att gga act gag ttt gga acg cca agc act acc tcc<br>Glu Asp Val Glu Ile Gly Thr Glu Phe Gly Thr Pro Ser Thr Thr Ser<br>                          285                                290                             295 | 975 |
| gcc cac cta gag tgg tgg atc aca aac ata aca cta act cct cta gat<br>Ala His Leu Glu Trp Trp Ile Thr Asn Ile Thr Leu Thr Pro Leu Asp<br>300                                305                                310 | 1023 |
| aga cct ctt att tcc taa atttcggcaa cctgggaatt atcaagttta<br>Arg Pro Leu Ile Ser<br>315 | 1071 |
| agaaaaggtg gagttgctaa agaattcaaa gaaaatttga aaagtaactt ttattgtgat | 1131 |
| ctc | 1134 |

<210> SEQ ID NO 5
<211> LENGTH: 319
<212> TYPE: PRT
<213> ORGANISM: Pyrococcus furiosus
<220> FEATURE:
<221> NAME/KEY: SIGNAL
<222> LOCATION: (1)..(19)
<223> OTHER INFORMATION:
<221> NAME/KEY: DOMAIN
<222> LOCATION: (28)..(49)
<223> OTHER INFORMATION: Linker Moiety
<221> NAME/KEY: DOMAIN
<222> LOCATION: (50)..(319)
<223> OTHER INFORMATION: Catalytic Domain

<400> SEQUENCE: 5

Met Ser Lys Lys Lys Phe Val Ile Val Ser Ile Leu Thr Ile Leu Leu
1                 5                     10                   15

Val Gln Ala Ile Tyr Phe Val Glu Lys Tyr His Thr Ser Glu Asp Lys
                   20                     25                     30

Ser Thr Ser Asn Thr Ser Ser Thr Pro Pro Gln Thr Thr Leu Ser Thr
                35                     40                     45

Thr Lys Val Leu Lys Ile Arg Tyr Pro Asp Asp Gly Glu Trp Pro Gly
    50                     55                     60

Ala Pro Ile Asp Lys Asp Gly Asp Gly Asn Pro Glu Phe Tyr Ile Glu

```
                65                  70                  75                  80
        Ile Asn Leu Trp Asn Ile Leu Asn Ala Thr Gly Phe Ala Glu Met Thr
                        85                  90                  95

Tyr Asn Leu Thr Ser Gly Val Leu His Tyr Val Gln Gln Leu Asp Asn
                        100                 105                 110

Ile Val Leu Arg Asp Arg Ser Asn Trp Val His Gly Tyr Pro Glu Ile
                        115                 120                 125

Phe Tyr Gly Asn Lys Pro Trp Asn Ala Asn Tyr Ala Thr Asp Gly Pro
                        130                 135                 140

Ile Pro Leu Pro Ser Lys Val Ser Asn Leu Thr Asp Phe Tyr Leu Thr
        145                 150                 155                 160

Ile Ser Tyr Lys Leu Glu Pro Lys Asn Gly Leu Pro Ile Asn Phe Ala
                        165                 170                 175

Ile Glu Ser Trp Leu Thr Arg Glu Ala Trp Arg Thr Thr Gly Ile Asn
                        180                 185                 190

Ser Asp Glu Gln Glu Val Met Ile Trp Ile Tyr Tyr Asp Gly Leu Gln
                        195                 200                 205

Pro Ala Gly Ser Lys Val Lys Glu Ile Val Pro Ile Ile Val Asn
                        210                 215                 220

Gly Thr Pro Val Asn Ala Thr Phe Glu Val Trp Lys Ala Asn Ile Gly
        225                 230                 235                 240

Trp Glu Tyr Val Ala Phe Arg Ile Lys Thr Pro Ile Lys Glu Gly Thr
                        245                 250                 255

Val Thr Ile Pro Tyr Gly Ala Phe Ile Ser Val Ala Ala Asn Ile Ser
                        260                 265                 270

Ser Leu Pro Asn Tyr Thr Glu Leu Tyr Leu Glu Asp Val Glu Ile Gly
                        275                 280                 285

Thr Glu Phe Gly Thr Pro Ser Thr Thr Ser Ala His Leu Glu Trp Trp
                        290                 295                 300

Ile Thr Asn Ile Thr Leu Thr Pro Leu Asp Arg Pro Leu Ile Ser
        305                 310                 315

<210> SEQ ID NO 6
<211> LENGTH: 12
<212> TYPE: PRT
<213> ORGANISM: Artificial Sequence
<220> FEATURE:
<223> OTHER INFORMATION: HSV-Tag

<400> SEQUENCE: 6

Ser Gln Pro Glu Leu Ala Pro Glu Asp Pro Glu Asp
1               5                   10

<210> SEQ ID NO 7
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 7
aggactccat atgaccgtcg agctgtcgg                                      29

<210> SEQ ID NO 8
<211> LENGTH: 28
<212> TYPE: DNA
<213> ORGANISM: Artificial Sequence
<220> FEATURE:
<223> OTHER INFORMATION: Synthetic Oligonucleotide
```

```
<400> SEQUENCE: 8
acctgagaag cttctgcacc gttacgga                                          28

<210> SEQ ID NO 9
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 9
agctccatat gtgcgactgg ctctttcc                                          28

<210> SEQ ID NO 10
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 10
acctgagaag cttctgcacc gttacgga                                          28
```

THERMOSTABLE CELLULASE

RELATED APPLICATIONS

This application is a continuation-in-part of and claims priority to PCT Application No. PCT/IS01/00012, filed Jun. 15, 2001 (in English), which is a continuation-in-part of U.S. application Ser. No. 09/594,884, filed Jun. 15, 2000 now abandoned; the entire teachings of the above applications are incorporated herein by reference.

BACKGROUND OF THE INVENTION

Cellulases are enzymes that are capable of hydrolyzing cellulose. The products of the reaction include cellobiose and glucose which can in used for a variety of applications. For example, glucose obtained by cellulase catalyzed hydrolysis of plant cellulose can be fermented to produce ethanol which can be used as a fuel.

Cellulases can also be used in the de-inking and refining of recycled paper. Enzymes with high thermal stability are particularly useful in these applications because elevated temperatures are commonly used in these processes. Thermostable cellulases are also useful in the consumer products and food industries, for example, in extracting and clarifying juice from fruits or vegetables. Cellulases and particularly thermostable cellulases also have applications in the textile and laundry industries. For example, the enzyme can be used to remove microfibers from the surface of cotton garments (or other garments made of cellulose based fabric), thereby brightening the color and removing the dull look that comes with wear. Cellulases are also useful for cleaning garments, for example as additives to detergents and for producing a "stone-washed" effect on indigo dyed denim (see, U.S. Pat. No. 4,912,056).

The development of thermostable cellulases with improved stability and/or catalytic properties would provide advantages for the above-referenced applications and certain other applications. Therefore, a need exists for improved thermostable cellulases which can be easily produced.

SUMMARY OF THE INVENTION

The invention relates to polypeptides having thermostable cellulase activity. The polypeptides of the invention are variants of full-length or naturally occurring proteins that have thermostable cellulase activity and are readily produced in large quantities by expression in a host cell such as *Escherichia coli*. In one embodiment, the polypeptide is a variant of a glycosyl hydrolase of family 12 wherein one or more of the amino acid residues that are not part of the catalytic domain (e.g, one or more amino acid residues in the amino terminal hydrophobic domain and/or linker moiety) are deleted. In preferred embodiments, the polypeptide is derived from a thermophilic organism from a *Rhodotermus* species such as *R. marinus, R. obamae,* and *R. obamensis*; or a *Pyrococcus* species, including *P. abyssi, P. endeavori, P. furiosus, P. horikoshi, P. shinkai,* and *P. woesei*. In a more particular embodiment, the polypeptide comprises the amino acid sequence of SEQ ID NO:2 wherein one or more of the amino acid residues from position one to about position 40 are deleted. In even more particular embodiments, the polypeptide can have an amino acid sequence selected from residues 18–261 of SEQ ID NO:2, residues 19–261 of SEQ ID NO:2, residues 20–261 of SEQ ID NO:2, residues 21–261 of SEQ ID NO:2, residues 22–261 of SEQ ID NO:2, residues 23–261 of SEQ ID NO:2, residues 24–261 of SEQ ID NO:2, residues 25–261 of SEQ ID NO:2, residues 26–261 of SEQ ID NO:2, residues 27–261 of SEQ ID NO:2, residues 28–261 of SEQ ID NO:2, residues 29–261 of SEQ ID NO:2, residues 30–261 of SEQ ID NO:2, residues 31–261 of SEQ ID NO:2, residues 32–261 of SEQ ID NO:2, residues 33–261 of SEQ ID NO:2, residues 34–261 of SEQ ID NO:2, residues 35–261 of SEQ ID NO:2, residues 36–261 of SEQ ID NO:2, residues 37–261 of SEQ ID NO:2 or residues 38–261 of SEQ ID NO:2.

The polypeptides of the invention can have improved catalytic properties and/or stability relative to full-length enzyme. In one embodiment, the polypeptide has a half-life of at least about 3.5 hours at 90° C. In another embodiment, the polypeptide has a specific activity that is at least about two times greater than the specific activity of a protein consisting of the amino acid sequence of SEQ ID NO:2.

In particularly preferred embodiments, the polypeptide has the amino acid sequence of residues 18–261 of SEQ ID NO:2 or the amino acid sequence of residues 38–261 of SEQ ID NO:2.

The invention also relates to isolated nucleic acids which encode a polypeptide of the invention and to constructs which comprises an isolated nucleic acid of the invention that is operatively linked to one or more regulatory sequences.

The invention also relates to host cells which comprise an isolated nucleic acid or construct of the invention, and to a method of producing a polypeptide having thermostable cellulase activity. In one embodiment, the method comprises maintaining a host cell of the invention under conditions suitable for expression of the polypeptide that has thermostable cellulase activity.

BRIEF DESCRIPTION OF THE DRAWINGS

The foregoing and other objects, features and advantages of the invention will be apparent from the following more particular description of preferred embodiments of the invention.

FIG. 2 is a photograph of an SDS-polyacrylamide gel stained with Coomassie brilliant blue G250. *E. coli* expression constructs encoding full-length Cel12A or variants thereof were induced and harvested 2.5 hours later. Crude cell contents were separated by SDS-PAGE and visualized by staining. Lane 1, uninduced culture; Lane 2, cells induced to express full-length Cel12A; Lane 3, cells induced to express Cel12A(sp-)H; Lane 4, cells induced to express δCel12AH.

DETAILED DESCRIPTION OF THE INVENTION

A description of preferred embodiments of the invention follows.

*Rhodothermus marinus* (*R. marinus*) is a thermophilic heterotrophic slightly halophilic marine eubacterium growing optimally at 65° C. *R. marinus* produces several thermostable glycosyl-hydrolases including a cellulase (Cel12A) (Hreggvidsson, G. O., et al., *Applied and Environmental Microbiology*, 62:3047–3049 (1996)), which has been cloned in *Escherchia coli* (*E. coli*) and characterised (Halldorsdottir, S. et al., *Appl Microbiol Biotechnol*, 49:277–284 (1998)). Cel12A, which belongs to family 12 glycosyl hydrolases, is among the most thermostable endocellulases, with maximal catalytic activity at temperatures substantially higher than the optimal temperature for growth of *R. marinus*. Many of cellulases in this family (family 12 glycosyl hydrolases) contain a highly hydrophobic signal peptide (Garda, A. L. et al., *Biochem J.*, 324:403–411 (1997); Ooi, T. et al., *Nucleic Acids Res.*, 18:5885 (1990)). Family 12 glycosyl-hydrolases catalyse the hydrolysis of β-1,4 glycosidic bonds primarily in mixed linkage (1-3),(1-4) β-D-glucans.

The invention relates to improved thermostable cellulases, nucleic acids and constructs (e.g., expression vectors) encoding the improved thermostable cellulases and to methods for producing the improved enzymes. As described herein, low yields of the thermostable cellulase Cel12A from *R. marinus* were obtained when a nucleic acid encoding the enzyme was expressed in *E. coli*. Low yields were obtained because the recombinant polypeptide was cytotoxic to the bacterial host cells. In addition, severe aggregation occurred when moderately high concentrations of the enzyme were heat treated at 65° C., which is the physiological temperature of *R. marinus*. Aggregation also occurred when the native protein was heated at 65° C. Analysis of the Cel12A sequence revealed that the protein, like certain other family 12 glycosyl hydrolases, comprises an amino terminal region that is highly hydrophobic (reminiscent of a signal peptide) and a catalytic domain which are linked by a linker moiety (e.g., region rich in proline, hydroxyamino acids (e.g., threonine, serine, tyrosine), alanine and/or glycine). Two variant polypeptides which lacked the amino-terminal hydrophobic region or the amino-terminal hydrophobic region and the linker moiety were produced in high yield when expressed in *E. coli*, indicating that cytotoxicity of Cel12A is mediated through the N-terminal hydrophobic region (putative signal peptide). The variant polypeptides were studied and their catalytic and physical properties compared to those of full-length Cel12A. The pH optima and substrate specificities of the variant polypeptides were the same as those of full-length Cel12A. However, the specific activities of the variants were about three fold higher than the specific activity of the full-length enzyme. Furthermore, the variant polypeptides were more stable than full-length Cel12A and had half-lives that exceeded 3 hours at 90° C. and unfolding temperatures that were up to about 103° C.

Polypeptides

In one aspect, the invention relates to polypeptides that have thermostable cellulase activity. Preferably the polypeptides of the invention can hydrolyze β-1,4 bonds in β-1,4-linked and mixed linkage β-glucans (e.g., carboxymethyl cellulose, cellulose). The polypeptides of the invention have the amino acid sequence of a thermostable cellulase wherein one or more amino acids which are not part of the catalytic domain of the enzyme are deleted. The catalytic domain and other domains (e.g., signal peptide, linker domains) of a cellulase can be readily identified by analysis and comparison of the amino acid sequence of a thermostable cellulase with the sequences of other cellulases (see, for example, Henrissat, B., *Biochem J*, 280:309–316 (1991); Henrissat, B. et al., *Biochem J*, 293:781–788 (1993)). For example, an amino acid sequence can be compared to the sequences in SWISS-PROT using a suitable comparison program, such as PROSITE (Hoffman, K. et al., *Nucleic Acids Res*, 27:215–219 (1999)).

In one example, the polypeptide of the invention can be a variant of a thermostable cellulase which contains an amino terminal hydrophobic region and a catalytic domain that are linked by a linker moiety (e.g., region rich in proline and/or hydroxylamino acids (e.g., threonine, serine, tyrosine)), such as certain family 12 glycosyl hydrolases (e.g., Cel12A from *R. marinus*, Eg1A from *Pyrococcus furiosus* and the like). The polypeptide of this example can have the amino acid sequence of the native or full-length cellulase (e.g., Cel12A, Eg1A) wherein one or more of the amino acids in the amino-terminal hydrophobic domain and/or linker moiety are deleted. Preferably, the polypeptide of this example has the amino acid sequence of the native or full-length cellulase wherein the amino acids which constitute the amino terminal hydrophobic region (e.g., signal peptide) or the amino acids which constitute the amino terminal hydrophobic region and the linker moiety are deleted. In certain embodiments, the deleted amino acid residues comprise a region in the range of at least the first 17 amino acid residues and up to the first 37 amino acid residues of the corresponding full-length polypeptide.

The nucleotide sequence of a nucleic acid encoding Cel12A of *Rhodothermus marinus* is deposited in GenBank under accession number U72637, the entire teaching of which are incorporated herein by reference. However, the originally deposited sequence contained sequence errors which have been rectified in the sequence depicted as (SEQ ID NO:1). Specifically, three nucleotides were missing, at positions 1019 (insert G), 1049 (insert C), 1093 (insert C), and positions 1467–68 CG should read GC and CG. The nucleic acid sequence (SEQ ID NO:1) has an open reading frame starting at position 710. The sequence of this open reading frame is presented herein as SEQ ID NO:3. The amino acid sequence of Cel12A of *Rhodothermus marinus* is presented herein as SEQ ID NO:2. The amino terminal hydrophobic domain of the protein (SEQ ID NO:2) consists of amino acid residues 1 to about 17, the amino acid residues from about position 18 to about position 37 constitute the linker moiety and the residues from about position 38 to position 261 constitute the catalytic domain. Note that due to the errors in the original DNA-sequence, the previously deposited amino acid sequence was erroneously assigned at residues 105–129.

In certain embodiments, the polypeptide of the invention has the amino acid sequence of Cel12A from *R. marinus* (SEQ ID NO:2) wherein one or more of the amino acid residues in the amino-terminal hydrophobic region and/or the linking moiety (positions 1 to about 40 of SEQ ID NO:2) are deleted. Preferably, the polypeptide of the invention has the amino acid sequence of SEQ ID NO:2 wherein at least about five or at least about ten amino acid residues in the amino-terminal hydrophobic region and/or the linking moiety are deleted. More preferably, the polypeptide of the invention has the amino acid sequence of SEQ ID NO:2 wherein at least about 15, or at least about 17, or at least about 20, or at least about 25, or at least about 30, or at least about 35 or about 37 of the amino acid residues in the amino-terminal hydrophobic region and/or the linking moiety are deleted. In additional embodiments, the polypeptide having thermostable cellulase activity has an amino acid sequence selected from the group consisting of residues 18–261 of SEQ ID NO:2, residues 19–261 of SEQ ID NO:2, residues 20–261 of SEQ ID NO:2, residues 21–261 of SEQ ID NO:2, residues 22–261 of SEQ ID NO:2, residues 23–261 of SEQ ID NO:2, residues 24–261 of SEQ ID NO:2, residues 25–261 of SEQ ID NO:2, residues 26–261 of SEQ ID NO:2, residues 27–261 of SEQ ID NO:2, residues 28–261 of SEQ ID NO:2, residues 29–261 of SEQ ID NO:2, residues 30–261 of SEQ ID NO:2, residues 31–261 of SEQ ID NO:2, residues 32–261 of SEQ ID NO:2, residues 33–261 of SEQ ID NO:2, residues 34–261 of SEQ ID NO:2, residues 35–261 of SEQ ID NO:2, residues 36–261 of SEQ ID NO:2, residues 37–261 of SEQ ID NO:2 and residues 38–261of SEQ ID NO:2. In more particular embodiments, the amino terminal amino acid residue of the polypeptide is methionyl. For example, the polypeptide can have the sequence of SEQ ID NO:2 wherein residues 2–17 or residues 2–37 are deleted. In another example, the amino acid sequence of the polypeptide is methionyl-residues 18–261 of SEQ ID NO:2 wherein the methionyl is the amino terminal residue of the polypeptide.

In a particularly preferred embodiment, the polypeptide having thermostable cellulase activity has the amino acid sequence of SEQ ID NO:2 wherein residues 2–17 or residues 2–37 are deleted.

Further encompassed by the present invention are thermostable cellulase active polypeptides with substantial sequence identity to SEQ ID NO: 2, wherein one or more of the first 37 amino acid residues of the full-length sequence are deleted, such as e.g., the first 17 amino acids (the hydrophobic amino terminal region), and/or a portion of or all of the linker moiety comprising residues from about 18–37. Substantial sequence identity in this context is meant to include at least about 85% identity, preferably at least about 90% identity, such as about 95% or 97% identity, and also including about 99% sequence identity. "Sequence identity" as used herein is calculated based on a reference sequence, (which in this instance is the sequence of SEQ ID NO: 2). Algorithms for sequence analysis are known in the art, such as BLAST, described in Altschul et al., *J. Mol. Biol.*, 215:403–10 (1990). Generally, the default settings with respect to e.g. "scoring matrix" and "gap penalty" will be used for alignment.

In additional embodiments, the polypeptide of the invention is a family 12 glycosyl hydrolase having the amino acid sequence of Eg1A from *Pyrococcus furiosus* (SEQ ID NO:5) wherein one or more of the amino acid residues in the amino-terminal hydrophobic region and/or the linking moiety are deleted. The nucleotide sequence (SEQ ID NO:4) of a nucleic encoding Eg1A from *Pyrococcus furiosus* is deposited in GenBank under accession number AF181032, the entire teaching of which are incorporated herein by reference. The nucleic acid sequence (SEQ ID NO:4) has an open reading frame starting at position 82. The amino acid sequence of Eg1A from *Pyrococcus furiosus* is presented herein as SEQ ID NO:5. The amino terminal hydrophobic domain of Eg1A consists of amino acid residues 1 to about 19 and the amino acid residues from about position 28 to about position 49 constitute the linker moiety (Bauer, M. W. et al., *J Bacteriology*, 181:284–290 (1999)). Accordingly, the polypeptide of the invention can comprise the amino acid sequence of residues 20 to 319 of SEQ ID NO:5 or the amino acid sequence of residues 50 to 319 of SEQ ID NO:5, for example.

Also encompassed by the present invention are thermostable cellulase active polypeptides with substantial sequence identity to SEQ ID NO: 5, wherein one or more of the first 49 amino acid residues (the hydrophobic amino terminal region and linker moiety) of the full-length sequence are deleted, such as e.g. the first 19 amino acids (the hydrophobic amino terminal region), and/or a portion of or all of the linker moiety comprising residues from about 20–49, where substantial sequence identity is defined as above.

The polypeptides of the invention can have improved characteristics, such as increased stability (e.g., thermal stability, detergent stability), increased solubility in aqueous solvents, increased catalytic activity (e.g., specific activity, catalytic rate) and/or reduced cytotoxicity relative to the native or full-length thermostable cellulase, but retain the substrate specificity of the native or full-length cellulase. Accordingly, the polypeptides of the invention provide many advantages over certain other thermostable cellulases. For example, as described herein large quantities of the polypeptides of the invention can be produced by expression in *E. coli*, or other host cells, including other bacterial cells, yeast cells or cells of a filamentous fungus. Examples of suitable bacterial cells besides *E. coli*, are *Bacillus spp., Lactobacillus spp.* and *Zymomomas spp.*; and of yeast cells are e.g., those of *Saccharomyces spp.* (particularly *S. cerevisiae*), *Schizosaccharomyces spp.*, and *Pichia spp.*; and useful cells of filamentous fungus include those from *Aspergillus spp.* such as *A. niger, A. nidulans* and *A. oryzae*; and *Neurospora spp.*, e.g., *Neurospora crassa*.

In one embodiment, the polypeptide of the invention has enhanced stability (e.g, thermal stability, detergent stability, longer shelf life) relative to the corresponding full-length cellulase. For example, the catalytic activity of the polypeptide of the invention can have a half-life that is about 1.5, about two or more times longer than the half-life of the full-length enzyme under certain conditions (e.g., storage at 4° C., heating to 90° C.). In a particular embodiment, the catalytic activity of the polypeptide of the invention has a half-life of at least about 2.5 hours at 90° C. Preferably, the catalytic activity of the polypeptide of the invention has a half-life of at least about 3 hours, or about 5 hours, or about 10 hours or more at 90° C.

In another embodiment, the polypeptide of the invention has enhanced specific activity relative to the corresponding full-length cellulase. For example, the specific activity of the polypeptide of the invention can be about 1.5 or about two or more times greater than the specific activity of the corresponding full-length cellulase. In a particular embodiment, the specific activity of the polypeptide of the invention is at least about two times greater than the specific activity of the corresponding full-length cellulase. Preferably, the specific activity of the polypeptide of the invention is at least about 3, or about 5 or more times greater than the specific activity of the corresponding full-length cellulase. The specific activity of the polypeptide of the invention and of full-length cellulases can be determined using any suitable method, such as the method described herein. Preferably, the specific activity is determined using carboxymethyl cellulose as the substrate.

The polypeptide of the invention can be a fusion protein comprising a polypeptide having thermostable cellulase activity as described herein which is fused to a second moiety not occurring in the cellulase as found in nature. Thus, the second moiety can be an amino acid, oligopeptide or polypeptide. The second moiety can be linked to the first moiety at a suitable position, for example, the N-terminus, the C-terminus or internally. In one embodiment, the fusion protein comprises an affinity ligand (e.g., an enzyme, an antigen, epitope tag (e.g., hemaglutinin (HA), HSV-Tag (SQPELAPEDPED (SEQ ID NO:6)), polyhistidine (e.g., His$_6$), a binding domain) as the first moiety, and a second moiety comprising a linker sequence and polypeptide that has thermostable cellulase activity as described herein. Additional (e.g., third, fourth) moieties can be present as appropriate. When the polypeptide is produced as a fusion protein, the fusion partner (e.g., HA, HSV-Tag, His$_6$) can be used to facilitate purification and/or isolation. If desired, the fusion partner can then be removed from polypeptide of the invention (e.g., by proteolytic cleavage).

Nucleic Acids and Constructs

The invention also relates to isolated nucleic acids and to constructs comprising the nucleic acids. The nucleic acids of the invention can be DNA or RNA, for example, mRNA. The nucleic acid molecules can be double-stranded or single-stranded; single stranded RNA or DNA can be either the coding, or sense, strand or the non-coding, or antisense, strand. Preferably, the nucleic acids encode a polypeptide of the invention. If desired, the nucleotide sequence of the isolated nucleic acid can include additional non-coding sequences such as non-coding 3' and 5' sequences (including regulatory sequences, for example). Additionally, the nucleic acids of the invention can be used to a nucleic acid comprising a marker sequence, for example, a nucleotide sequence which encodes a polypeptide to assist in isolation or purification of the polypeptide. Representative sequences include, but are not limited to, those which encode a glutathione-S-transferase (GST) fusion protein, a polyhistidine (e.g., His$_6$), hemagglutinin, HSV-Tag, for example.

The nucleic acid molecules of the invention are "isolated" as used herein, an "isolated" nucleic acid molecule or nucleotide sequence is intended to mean a nucleic acid molecule or nucleotide sequence which is not flanked by nucleotide sequences which normally flank the gene or nucleotide sequence (as in genomic sequences) and/or has been completely or partially purified from other nucleic acids (e.g., as in an DNA or RNA library). For example, an isolated nucleic acid of the invention may be substantially isolated with respect to the complex cellular milieu in which it naturally occurs. In some instances, the isolated material will form part of a composition (for example, a crude extract containing other substances), buffer system or reagent mix. In other circumstance, the material may be purified to essential homogeneity, for example as determined by PAGE or column chromatography such as HPLC. Thus, an isolated nucleic acid molecule or nucleotide sequence can include a nucleic acid molecule or nucleotide sequence which is synthesized chemically, using recombinant DNA technology or using any other suitable method. Therefore, a recombinant nucleic acid (e.g., DNA, RNA) contained in a vector is included in the definition of "isolated" as used herein. Also, isolated nucleotide sequences include recombinant nucleic acid molecules (e.g., DNA, RNA) in heterologous organisms, as well as partially or substantially purified nucleic acids in solution. In vivo and in vitro RNA transcripts of a DNA molecule of the present invention are also encompassed by "isolated" nucleotide sequences.

The present invention also pertains to nucleotide sequences which are not necessarily found in nature but which encode a polypeptide of the invention. For example, DNA molecules which comprise a sequence which is different from the naturally-occurring nucleotide sequence (e.g., SEQ ID NO:3) but which, due to the degeneracy of the genetic code, encode a polypeptides of the invention are the subject of this invention. The invention also encompasses variations of the nucleotide sequences of the invention, such as those encoding active fragments or active derivatives of the polypeptides as described below. Such variations can be naturally-occurring, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions. Preferably, the nucleotide or amino acid variations that are within the catalytic domain are silent or conserved; that is, they do not alter the improved characteristics or activity of the encoded polypeptide.

The invention described herein also relates to fragments of the isolated nucleic acid molecules described herein. The term "fragment" is intended to encompass a portion of a nucleotide sequence described herein which is from at least about 25 contiguous nucleotides to at least about 50 contiguous nucleotides or longer in length; such fragments are useful as probes and also as primers. Particularly preferred primers and probes selectively hybridize to the nucleic acid molecule encoding the polypeptides described herein. For example, fragments which encode polypeptides that retain activity, as described below, are particularly useful.

The invention also pertains to nucleic acid molecules which hybridize under high stringency hybridization conditions, such as for selective hybridization, to a nucleotide sequence described herein (e.g., nucleic acid molecules which specifically hybridize to a nucleotide sequence encoding polypeptides described herein and encode a polypeptide having thermostable cellulase activity). Hybridization probes include synthetic oligonucleotides which bind in a base-specific manner to a complementary strand of nucleic acid. Suitable probes include polypeptide nucleic acids, as described in Nielsen et al., *Science*, 254:1497–1500 (1991).

Such nucleic acid molecules can be detected and/or isolated by specific hybridization (e.g., under high stringency conditions). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 60%, 75%, 85%, 95%). For example, certain high stringency conditions can be used which distinguish perfectly complementary nucleic acids from those of less complementarity.

"High stringency conditions", "moderate stringency conditions" and "low stringency conditions" for nucleic acid hybridizations are explained on pages 2.10.1–2.10.16 and pages 6.3.1–6 in *Current Protocols in Molecular Biology* (Ausubel, F. M. et al., "*Current Protocols in Molecular Biology*", John Wiley & Sons, (1998)) the teachings of which are hereby incorporated by reference. The exact conditions which determine the stringency of hybridization depend not only on ionic strength (e.g., 0.2×SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions can be determined empirically.

By varying hybridization conditions from a level of stringency at which no hybridization occurs to a level at which hybridization is first observed, conditions which will allow a given sequence to hybridize (e.g., selectively) with the most similar sequences in the sample can be determined.

Exemplary conditions are described in Krause, M. H. and S. A. Aaronson, *Methods in Enzymology*, 200:546–556 (1991). Also, in, Ausubel, et al., "*Current Protocols in Molecular Biology*", John Wiley & Sons, (1998), which describes the determination of washing conditions for moderate or low stringency conditions. Washing is the step in which conditions are usually set so as to determine a minimum level of complementarity of the hybrids. Generally, starting from the lowest temperature at which only homologous hybridization occurs, each degree (° C.) by which the final wash temperature is reduced (holding SSC concentration constant) allows an increase by 1% in the maximum extent of mismatching among the sequences that hybridize. Generally, doubling the concentration of SSC results in an increase in $T_m$ of –17EC. Using these guidelines, the washing temperature can be determined empirically for high, moderate or low stringency, depending on the level of mismatch sought.

For example, a low stringency wash can comprise washing in a solution containing 0.2×SSC/0.1% SDS for 10 min at room temperature; a moderate stringency wash can comprise washing in a prewarmed solution (42° C.) solution containing 0.2×SSC/0.1% SDS for 15 min at 42° C.; and a high stringency wash can comprise washing in prewarmed (68° C.) solution containing 0.1×SSC/0.1% SDS for 15 min at 68° C. Furthermore, washes can be performed repeatedly or sequentially to obtain a desired result as known in the art.

Equivalent conditions can be determined by varying one or more of the parameters given as an example, as known in the art, while maintaining a similar degree of identity or similarity between the target nucleic acid molecule and the primer or probe used. Hybridizable nucleotide sequences are useful as probes and primers for identification of organisms (e.g., recombinant bacteria) containing a nucleic acid of the invention and to isolate a nucleic acid of the invention, for example. As used herein, the term "primer" refers to a single-stranded oligonucleotide (e.g., synthetic oligo deoxyribonucleotide) which acts as a point of initiation of template-directed DNA synthesis under appropriate conditions (e.g., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. The term "primer site" refers to the area of the target DNA to which a primer hybridizes. The term "primer pair" refers to a set of primers including a 5' (upstream) primer that hybridizes with the 5' end of the DNA sequence to be amplified and a 3' (downstream) primer that hybridizes with the complement of the 3' end of the sequence to be amplified.

The invention also pertains to nucleotide sequences which have substantial identity with the nucleotide sequences described herein; particularly preferred are nucleotide sequences which have at least about 10%, preferably at least about 20%, more preferably at least about 30%, more preferably at least about 40%, even more preferably at least about 50%, yet more preferably at least about 70%, still more preferably at least about 80%, and even more preferably at least about 90% or 95% identity, with nucleotide sequences described herein. Particularly preferred in this instance are nucleotide sequences encoding polypeptides having thermostable cellulase activity and an amino acid sequence described herein.

To determine the percent identity of two nucleotide sequences, the sequences can be aligned for optimal comparison purposes (e.g., gaps can be introduced in the sequence of a first nucleotide sequence). The nucleotides at corresponding nucleotide positions can then be compared. When a position in the first sequence is occupied by the same nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent identity between two sequences can be accomplished using a mathematical algorithm. A preferred, non-limiting example of a mathematical algorithm utilized for the comparison of two sequences is the algorithm of Karlin et al., *Proc. Natl. Acad. Sci. USA*, 90:5873–5877 (1993). Such an algorithm is incorporated into the NBLAST program which can be used to identify sequences having the desired identity to nucleotide sequences of the invention. To obtain gapped alignments for comparison purposes, Gapped BLAST can be utilized as described in Altschul et al., *Nucleic Acids Res,* 25:3389–3402 (1997). When utilizing BLAST and Gapped BLAST programs, the default parameters of the respective programs (e.g., NBLAST) can be used. See http://www.ncbi.nlm.nih.gov. In one embodiment, parameters for sequence comparison can be set at W=12. Parameters can also be varied (e.g., W=5 or W=20). The value "W" determines how many continuous nucleotides must be identical for the program to identify two sequences as containing regions of identity.

In certain embodiments, the isolated nucleic acid encodes a polypeptide having the amino acid sequence of Cel12A from *R. marinus* (SEQ ID NO:2) wherein one or more of the amino acid residues in the amino-terminal hydrophobic region and/or the linking moiety (positions 1 to about 37 of SEQ ID NO:2) are deleted. Preferably, the isolated nucleic acid encodes a polypeptide having the amino acid sequence of SEQ ID NO:2 wherein at least about five or at least about ten amino acid residues in hydrophobic region and/or the linking moiety are deleted. More preferably, the isolated nucleic acid encodes a polypeptide having the amino acid sequence of SEQ ID NO:2 wherein at least about 15, or at least about 17, or at least about 20, or at least about 25, or at least about 30, or at least about 35 or about 37 of the amino acid residues in hydrophobic region and/or the linking moiety are deleted. In additional embodiments, the isolated nucleic acid of the invention encodes a polypeptide having thermostable cellulase activity, and has a nucleotide sequence selected from the group consisting of nucleotides 52–783 of SEQ ID NO:3, nucleotide 55–783 of SEQ ID NO:3, nucleotides 58–783 of SEQ ID NO:3, nucleotides 61–783 of SEQ ID NO:3, nucleotides 64–783 of SEQ ID NO:3, nucleotides 67–783 of SEQ ID NO:3, nucleotides 70–783 of SEQ ID NO:3, nucleotides 73–783 of SEQ ID NO:3, nucleotides 76–783 of SEQ ID NO:3, nucleotides 79–783 of SEQ ID NO:3, nucleotides 82–783 of SEQ ID NO:3, nucleotides 85–783 of SEQ ID NO: 3, nucleotides 88–783 of SEQ ID NO: 3, nucleotides 91–783 of SEQ ID NO:3, nucleotides 94–783 of SEQ ID NO:3, nucleotides 97–783 of SEQ ID NO:3, nucleotides 100–783 of SEQ ID NO:3, nucleotides 103–783 of SEQ ID NO:3, nucleotides 106–783 of SEQ ID NO:3, nucleotides 109–783 of SEQ ID NO:3 and nucleotides 112–783 of SEQ ID NO:3. In more particular embodiments, the amino terminal amino acid residue of the polypeptide is methionyl. Accordingly, the isolated nucleic acid of the invention can have the sequence atg-nucleotides 52–783 of SEQ ID NO:3 or atg-nucleotides 112–783 of SEQ ID NO:3, for example. In a particularly preferred embodiment, the isolated nucleic acid encoding a polypeptide having thermostable cellulase activity has the sequence of nucleotides 52–789 of SEQ ID NO:3 or nucleotides 112–783 of SEQ ID NO:3.

In additional embodiments, the isolated nucleic acid of the invention encodes a family 12 glycosyl hydrolase having the amino acid sequence of Eg1A from *Pyrococcus furiosus* wherein one or more of the amino acid residues in the amino-terminal hydrophobic region and/or the linking moiety are deleted. For example, the isolated nucleic acid can have the sequence of nucleotides 139–1041 of SEQ ID NO:4 or the sequence of nucleotides 229–1041 of SEQ ID NO:4.

The nucleic acids described herein can be amplified by methods known in the art. For example, amplification can be accomplished by the polymerase chain reaction (PCR). See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19:4967 (1991); Eckert et al., *PCR Methods and Applications* 1, 17 (1991); PCR (eds. McPherson et al., IRL Press, Oxford); and U.S. Pat. No. 4,683,202. Other suitable amplification methods include the ligase chain reaction (LCR) (see Wu and Wallace, *Genomics*, 4:560 (1989), Landegren et al., *Science*, 241:1077 (1988), transcription amplification (Kwoh et al., *Proc. Natl. Acad. Sci. USA*, 86:1173 (1989)), and self-sustained sequence replication (Guatelli et al., *Proc. Nat. Acad. Sci. USA*, 87:1874 (1990)) and nucleic acid based sequence amplification (NASBA).

The invention includes recombinant constructs comprising an isolated nucleic acid as described herein operably linked to at least one regulatory sequence. Generally, the isolated nucleic acid is joined (e.g., ligated, inserted) to a suitable vector, such as a plasmid or viral vector that includes an origin of replication, a selectable genetic marker and/or sequences which allow the insert nucleic acid to be expressed (transcribed and/or translated). For example the recombinant construct can be an expression vector containing a nucleic acid sequence encoding a polypeptide described herein that is operably linked to at least one regulatory sequence. Many expression vectors are commercially available, and other suitable vectors can be readily prepared by the skilled artisan. As used herein, "operably linked" means that the nucleotide sequence is linked to a regulatory sequence in a manner which allows expression (e.g., transcription and/or translation) of the nucleic acid sequence. Regulatory sequences are art-recognized and are selected to produce the polypeptide or active derivative or fragment thereof. Accordingly, the term "regulatory sequence" includes promoters, enhancers, ribosome binding sites, polyadenylation signals and other expression control elements which are described, for example, in Goeddel, *Gene Expression Technology: Methods in Enzymology* 185, Academic Press, San Diego, Calif. (1990). For example, regulatory sequences native to *R. marinus* can be employed to express Cel12A. Suitable expression vectors and regulatory elements can be selected to provide for the desired level of expression in a desired host cell. For example, the polypeptides of the present invention can be produced by ligating a nucleic acid encoding the polypeptide into a vector suitable for expression in an appropriate host cell (see, for example, Broach, et al., *Experimental Manipulation of Gene Expression*, ed. M. Inouye (Academic Press, 1983) p. 83; *Molecular Cloning: A Laboratory Manual*, 2nd Ed., ed. Sambrook et al. (Cold Spring Harbor Laboratory Press, 1989) Chapters 16 and 17)). For example, where expression in *E. coli* is desired the vector can include the T7/lac promotor. Other suitable regulatory sequences for use in *E. coli*, other bacteria, fungi (yeast, molds), insect and/or mammalian cells are known in the art. Typically, expression constructs contain one or more suitable selectable markers. Suitable selectable genetic markers include, for example, genes which confer resistance to antibiotics such as the β-lactamase gene from Tn3, the kanamycin-resistance gene from Tn903, the chloramphenicol-resistance gene from $Tn_9$, and the like. Suitable origins or replication include, for example, Ori p, colE1 Ori and the like.

Recombinant Host Cells and Methods of Production

The invention also relates to recombinant host cells (e.g., prokaryotic, eukaryotic, archaeon) which comprise an expression vector or isolated nucleic acid as described herein. For example, cells which can comprise a vector or isolated nucleic of the invention (for example, as a result of transformation, transfection or tranduction) include, but are not limited to, bacterial cells (e.g., *R. marinus, E. coli* (e.g., *E. coli* K12 strains), *Streptomyces, Pseudomonas, Bacillus, Serratia marcescens, Salmonella typhimurium*), fungi including yeasts (e.g., *Saccharomycies cerevisie, Pichia pastoris*) and molds (e.g., *Aspergillus sp.*), insect cells (e.g., Sf9) or mammalian cells (e.g., COS, CHO). The construct (e.g., expression vector) can be introduced into the host cells using any suitable method (e.g., electroporation, transfection using calcium chloride, rubidium chloride, calcium phosphate, DEAE-dextran, or other substances; microprojectile bombardment; lipofection, infection, transduction).

The isolated nucleic acid molecules and vectors of the invention are useful in the manufacture of the encoded polypeptide, as probes for isolating homologous sequences (e.g., from other bacteriophage species), as well as for detecting the presence of a nucleic acid of the invention in a cells.

The invention also relates to a method of producing (in vitro, in vivo) a polypeptide having thermostable cellulase activity. For example, a nucleic acid encoding a polypeptide of the invention, or a construct comprising such nucleic acid, can be introduced into a suitable host cell by a method appropriate to the host cell selected (e.g., transformation, transfection, electroporation, infection), such that the nucleic acid is operably linked to one or more expression control elements (e.g., in a vector, in a construct created by processes in the cell, integrated into the host cell genome). Host cells can be maintained under conditions suitable for expression (e.g., in vivo or in vitro, in the presence of inducer, suitable media supplemented with appropriate salts, growth factors, antibiotic, nutritional supplements, etc.), whereby the encoded polypeptide is produced. In additional embodiments, the polypeptide of the invention can be produced by in vitro translation of a nucleic acid that encodes the polypeptide (e.g., a nucleic acid having a sequence described herein), by chemical synthesis (e.g., solid phase peptide synthesis) or by any other suitable method. If desired, the polypeptide having thermostable cellulase activity can be isolated (e.g., from the host cells, medium, milk). It will be appreciated that the method encompasses expression of the polypeptide in a host cell of a transgenic animal or plant (see e.g., U.S. Pat. Nos. 6,013,857, 5,990385, 5,994,616).

Uses for Polypeptides that have Thermostable Cellulase Activity

The polypeptides of the invention are useful in a variety of applications, such as industrial processes. For example, the polypeptides can be used to improve freeness and to remove inks, coatings, toners and colors from wood or paper pulp (see, e.g., U.S. Pat. Nos. 6,066,233, 5,525,193 and WO 98/44189). The polypeptides of the invention can also be included in detergent compositions and to treat cellulose-containing textiles and garments to improve the feel of the fabric or to remove lint, for example (see, e.g., U.S. Pat. Nos. 5,904,736, 5,792,641, 5,445,957). Additional uses for the polypeptides of the invention are in the treatment of fibrous crops, fruits and vegetables or grains to improve feed values or to extract starches (e.g., sugars) or other components of the crop, fruit, vegetable or grain being treated. A number of methods for treating crops, fruits, vegetables or grains with a cellulase are known in the art (see, e.g., U.S. Pat. Nos. 5,948,454, 4,795,101, 4,371,552 and WO 97/23652).

EXAMPLE

Materials and Methods

Bacterial Strains

Nova Blue and BL21 (DE3) strains of *E. coli* (Novagen, Madison, Wis.) were used for cloning and expression of variants of Cel12A. The GE2205 (Institute of Biology, University of Iceland) strain of *E. coli* containing plasmid pET23bAH was used for expression of a cel12A gene (Halldorsdottir, S. et al., *Appl Microbiol Biotechnol*, 49:277–284 (1998)). Plasmid pET25b(+) (Novagen) was used for expression of variants of the Cel12A protein.

Construction of Plasmids and Sequencing

A gene fragment encoding 223 amino acids of the Cel12A (starting at the 38th amino acid), named δ cel12A with introduced NdeI and HindIII restriction sites was obtained by PCR utilising pET23bAH plasmid (Halldorsdotfir, S. et al., *Appl Microbiol Biotechnol*, 49:277–284 (1998)) as a template. The following primers were used for amplification of δ cel12A: forward synthetic oligonucleotide primer (NdeI site underlined): 5'-AGGACTCCATATGACCGTCGA-GCTGTCGG-3' (SEQ ID NO:7), reverse synthetic oligonucleotide primer (HindIII site underlined): 5'-ACCTGAG AAGCTTCTGCACCGTTACGGA-3' (SEQ ID NO:8). AmpliTaq Gold™ (Perkin-Elmer AB, Foster City, Calif.) DNA polymerase and hot start PCR protocol of 35 cycles of denaturation at 95° C. for 1 min, annealing at 60° C. for 1 min and primer extension at 72° C. for 1 min were used. PCR fragments were separated by agarose gel electrophoresis, purified using a QIAEX II kit (QIAGEN GmbH, Hilden, Germany), digested overnight with Nde I and Hind III and purified again using the QIAEX II kit.

The gene fragment encoding Cel12A with the amino terminal hydrophobic region (putative signal peptide (first 17 amino acids)) deleted, named cel12A(sp-) was amplified using the following primers: forward synthetic oligonucleotide primer (NdeI site underlined): 5'-AGCTC CATATGTGCGACTGGCTCTTTCC-3' (SEQ ID NO:9) and reverse synthetic oligonucleotide primer (HindIII site underlined): 5'-ACCTGAGAAGCTTCTGCACCGTTAC-GGA-3' (SEQ ID NO:10) and purified as described above. The pET25b(+) vector was opened with restriction enzymes (Nde I and Hind III) and purified using QIAEX II kit. Inserts were cloned into appropriately opened vectors to produce plasmids: pET25δCel12AH and pET25Cel12A(sp-)H.

Plasmids were prepared using QIAGEN Mini Plasmid Kit. The presence of cloned inserts in the plasmids was confirmed by restriction analysis and partial sequencing by the dideoxy chain termination method using the ABI PRISM Dye Terminator Cycle Sequencing Ready Reaction (Perkin-Elmer).

All restriction enzymes and T4 ligase were from Life Technologies (Rockville, Md.). The enzymes were used according to the manufacture's protocols.

Culture Conditions and Protein Production

For expression of variant forms of the cellulase, bacteria were grown in baffled flasks in LB medium containing ampicilin to $OD_{600}=0.7$ and then induced with IPTG (final concentration 1 mM). Growth was continued for an additional 2.5–3 hours. Cells were harvested by centrifugation. The cell pellet was resuspended in 20 mM Tris-HCl pH 7.4/20 mM imidazole/0.5 M NaCl buffer. Disintegration of the cells was performed using a UP400S sonicator (Dr. Heilscher GmbH, Stahnsdorf, Germany) at 60 W $cm^{-2}$, 3×120 seconds on ice. The crude cell extract was centrifuged at 27,000× g for 20 min at 4° C. and the supernatant stored frozen in −20° C. for later purification.

Fed-batch cultivation for production of the Cel12A protein was carried out as described (Nordberg, K. E. et al., *J. Ferment. Bioeng.*, (in press, 2000)). Bacteria were grown until the $OD_{600}$ reached 32 and induced by addition of IPTG (final concentration 0.5 mM). Growth was continued for an additional 90 min. Whole fermentation culture was run three times on a Gaulin high-pressure homogenizer (APV-Schr öder GmbH, Lübeck, Germany) at 700 atm to disintegrate the cells. The cell extract was centrifuged (27,000× g, 4° C., 15 min) and the supernatant frozen at −20° C. and stored for purification.

Protein Purification

Crude cell extracts containing variant Cel12A proteins were heat-treated at 65° C. for 30 min, centrifuged at 27,000× g for 15 min and the supernatants were loaded onto a chromatography column (crude extracts containing full-length Cel12A were not heat-treated). Recombinant proteins were purified utilizing C-terminal 6×Hisidine tags and immobilized metal-ion affinity chromatography (IMAC) as described (Abou-Hachem et al., *Biochem. J.*, 345:53–60 (2000)). The eluate was dialyzed three times for several hours, against 45 volumes of 20 mM Tris-HCl pH 7.5 in dialysis tubes with a molecular weight cut-off of 3.5 kD. Proteins were concentrated using Aquacide III (CALBIOCHEM, La Jolla, Calif.) according to the manufacture's protocol. Then, the concentrated protein solutions were centrifuged and the supernatants were stored at 4° C. until used for further testing.

The histidine tag was removed from the purified polypeptides by digestion with carboxypeptidase-A type II from bovine pancreas (Sigma) for 1 hour at 37EC. Following digestion, the polypeptide solutions were loaded onto the affinity column and portions which did not bind (flow through) were collected. A portion of the flow through was analysed by SDS-PAGE to verify that the histidine tag had been removed.

Gel filtration chromatography was used to separate of cleaved and uncleaved Cel12A(sp-)H protein. A 50 cm column with internal diameter of 17 mm (Biorad), packed with Sephadex G-50 resin (Amersham Pharmacia Biotech AB, Uppsala, Sweden) was used. The column was run using 20 mM Tris-HCl pH 7.5.

Protein Characterization

Protein production was analysed by sodium dodecyl sulphate polyacrylamide electrophoresis (SDS-PAGE) in 12.5% gels using the method of Laemmli (Laemmli, U. K., *Nature*, 227:680–685 (1970)). Proteins were visualized by staining with Coomassie brilliant blue G250 (Merck, Darmstadt, Germany). Enzyme activity was detected using a 1% (w/v) agarose overlayer gel containing 0.02% (w/v) carboxymethyl cellulose (CMC). The SDS/PAGE gels were washed with phosphate buffer pH 7.0 containing 1% Triton X-100 (t-octylphenoxypolyethoxyethanol, Merck) for 20 min. Thereafter, the gels were washed with phosphate buffer pH 7.0, covered with the overlayer gel and incubated for 2 hours at 65° C. Then, the agarose gels were stained in 1% (w/v) Congo red solution. Excess dye was removed by washing with 1 M NaCl.

The dinitrosalicylic acid (DNS) stopping method was used for enzyme activity measurements. Samples were incubated with 0.9% (w/v) CMC in 20 mM Tris-HCl pH 7.5 at 65° C. for about 20 minutes or about 30 minutes. The enzymatic reactions were stopped by adding 1.5 volume of DNS-solution (1% DNS/0.2% phenol/0.05% $Na_2SO_3$/1% NaOH/20% Na.K.tartrate) to the samples and boiling the samples for 15 minutes. The amount of reducing sugars released was measured in 96 well microtiter plates by absorbance at 550 nm, using glucose solutions as standards.

CMC, phosphoric acid swollen cellulose (PASC), birch wood xylan, lichenan, locust bean gum and guar gum (all SIGMA, St. Louis, Mo.) and Konjak (Megazyme International Ltd.) were used for enzyme substrate specificity tests. Temperature optima were determined by running the activity assay at different temperatures ranging from 40° C. to 105° C. in 20 mM Tris-HCl pH 7.5 for 20 minutes. pH optima were studied by running the activity assay in 0.1 M citrate/phosphate buffer (pH ranging from 3.0 to 6.0), 0.1 M sodium phosphatebuffer (pH ranging from 6.0 to 7.0), 50 mM Tris-HCl buffer (pH ranging from 7.0 to 9.0) and glycine-NaOH buffer (pH ranging from 9.0 to 10.0) at 65° C. for 30 min. Temperature stability was examined by determining residual enzymatic activity after incubating the proteins in absence of substrates at 65° C., 85° C. and 90° C. for predetermined periods of time.

DNA and Protein Sequence Analysis

A few Internet data banks and net tools were utilized for primary sequence analysis and secondary and tertiary structure prediction. BLAST 2.0 (Altschul et al., *Nucleic Acids Research*, 25:3389–3402 (1997); Altschul et al., *J Mol Bio*, 215:403–410 (1990)) which is available on a server of the National Center for Biotechnology Information—http://www.ncbi.nlm.nih.gov/) was used to investigate related sequences. Primary structure analysis was done using tools and databases available on the ExPASy Molecular Biology Server (http://www.expasy.ch/), such as PROSITE (Hofmann et al., *Nucleic Acids Research*, 27:215–219 (1999); Bairoch A., *Nucleic Acids Research* 20 *Suppl.*:2013–2018 (1992)) and SignalP (Nielsen H. et al. *Protein Engineering*, 10:1–6 (1997)).

Differential Scanning Calorimetry (DSC)

Thermal transitions were measured by DSC using a VP-DSC microcalorimeter (MicroCal Inc., Northampton, Mass.), and the following parameters: scan rate 60° C./h and temperature range from 25° C. to 130° C. Different protein concentrations (ranging from 0.1 to 0.4 mg/ml) were used and measurements were perfomed in 20 mM Tris-HCl pH 7.5. Additional measurements were made using the same Tis buffer supplemented with 1 mM $CaCl_2$, 0.5% CMC or 0.5% SDS.

Results

Expression of Full Length Cel12A in *E. coli*

Figure 1:
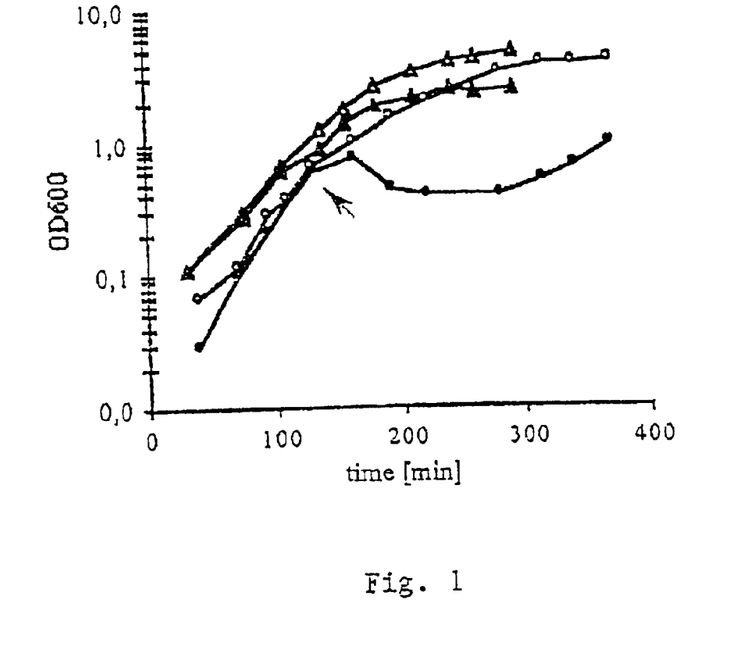
FIG. 1 is a graph illustrating the growth of *Escherichia coli* (*E. coli*) strain BL21(DE3) transfected with constructs encoding full-length Cel12A or δCEL12AH. Expression of Cel12A or δCEL12AH was induced by adding isopropyl β-D-thio-galactopyranoside (IPTG) to the cultures (time of addition of IPTG marked with the arrow). Cultures containing cells transfected with the construct encoding full-length Cel12A were induced (●) or not induced (○), and cultures containing cells transfected with the construct encoding δCEL12AH were induced (▲) or not induced (△). Induction of expression of full-length Cel12A (●) resulted in a decrease in the $OD_{600}$.
Figure 2:
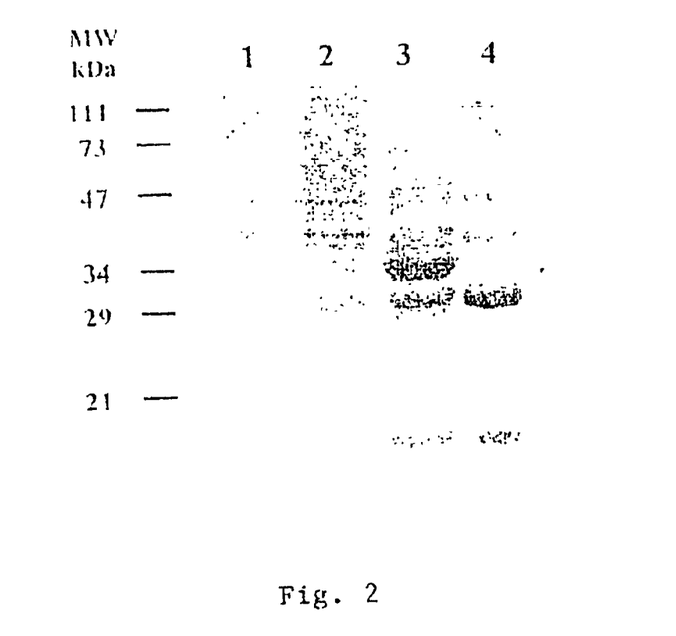

Cultivation of *E. coli* transformed with an expression plasmid encoding full length Cel12A in a shake-flask, revealed that induction of expression of the recombinant protein resulted in a decrease in optical density measured at 600 nm (FIG. 1), indicating that full length Cel12A induced cell lysis. Significant changes in bacterial morphology were noted after induction of Cel12A expression. Notably, the cultures contained mostly long (up to 30 fold longer than normal *E. coli* cell) filamentous bacteria and multiple-cell clumps. Production of the cellulase (i.e., Cel12A) was extremely low due to the toxicity of the full length protein, and no clear recombinant protein band was visible on SDS-polyacrylamide gels (FIG. 2). However, two faint bands were detected on an activity stained over-layer gel. The second band detected using the activity over-layer gel was probably produced by cleavage of Cel12A within linker region by bacterial proteases. Similar results were obtained when full length Cel12A was expressed in *E. coli* at 30° C. Specifically, no Cel12A was detected by SDS-PAGE, however no significant decrease in optical density was noticed.

To obtain enough protein for further tests the protein was produced using fed-batch cultivation. However, induction of expression at high cell density led to a decrease in optical density that was associated with intensive foaming and increased culture viscosity, hallmarks of cell lysis. As in the shake-flask cultures, outgrowth of bacteria was eventually observed in cultures maintained under growth conditions. The cultivation was stopped 2.5 hours after induction. Enzymatic activities (measured with DNS-stopping method) found in the cell pellet and in the supernatant were about equal. Thus, the Cel12A protein was purified from the entire batch culture (cells and media) to avoid protein lost. The Cel12A was purified by IMAC chromatography without prior heat-treatment of crude cell extract. Partially purified protein was then heat-treated. Intensive precipitation of recombinant protein occurred upon heating, resulting in very low yield of pure Cel12A.

The purified full length Cel12A protein was not stable at 4° C. and lost activity after several weeks of storage.

Sequence Analysis of the Cel12A Gene

Figures 3A, 3B, 3C, 3D:
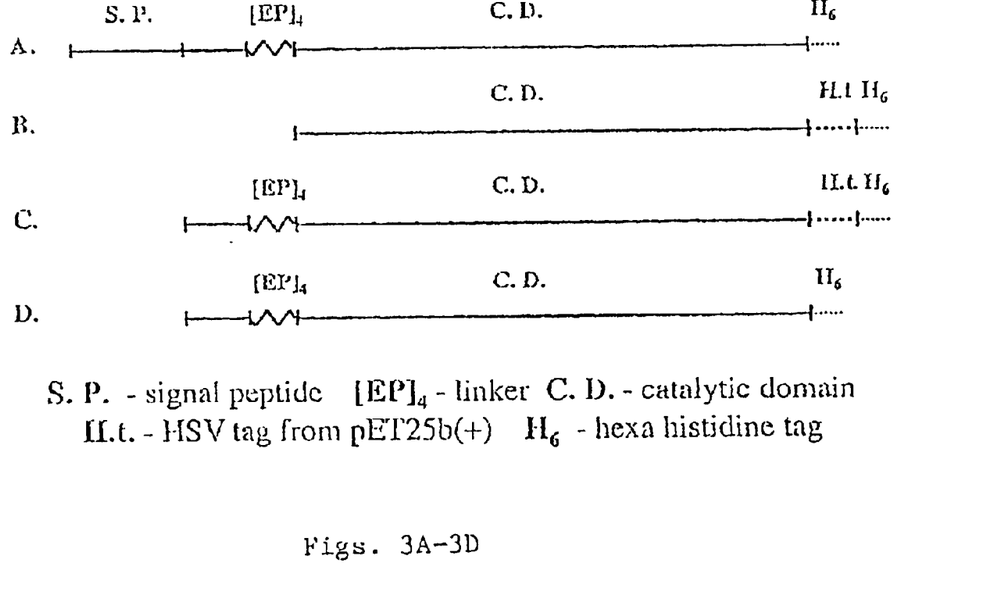
FIGS. 3A–3D are schematic representations of full-length Cel12A (A) and variants δCel12AH (B), Cel12A(sp-)H (C) and Cel12A(sp-) (D). S.P.-signal peptide. [EP]$_4$-linker moiety. C.D.-catalytic domain. H.t.-HSV-Tag. H6-hexahistidine.
Figure 4:
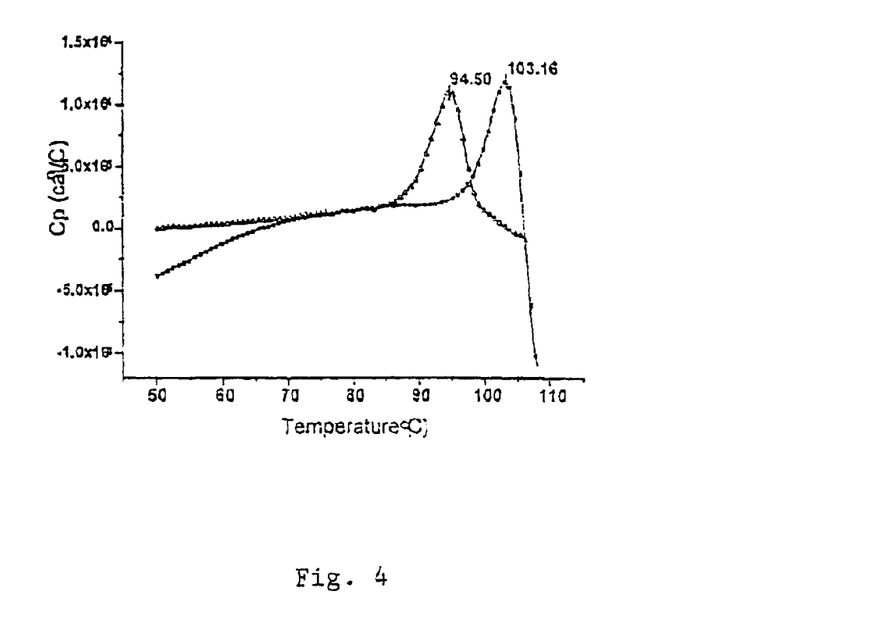
FIG. 4 is a graph showing the thermal unfolding curves for Cel12A(sp-)H (■) and δCel12AH (△) measured by differential scanning calorimetry.

Properties of the Cel12A based on sequence analysis were predicted using ProtScale (http://www.expasy.ch/cgi-bin/protscale.pl). Amino acid sequence profiling using an optimised matching hydrophobicity (OMH) scale (Sweet, R. M. et al., *J Mol Biol*, 171:479–488 (1983)) demonstrated that the N-terminal part of Cel12A is the most hydrophobic region of the molecule. This hydrophobic region is connected to a short and less hydrophobic region. Profiling using the average flexibility index (Bhaskaran, R. et al., *Int J Pept Protein Res*, 32:242–255 (1988)) showed that the first several amino acids of the protein (amino terminal amino acids) could form highly rigid secondary structure in the protein. Additionally, the hydrophobic amino terminal region was followed by the most flexible region of the protein. The flexible region comprises a doublet of glutamic acid and proline that is repeated four times ($[EP]_4$). These studies revealed that Cel12A includes a catalytic domain and a hydrophobic N-terminal region that are linked through a flexible linker moiety (FIG. 3A). The amino-terminal region (first 38 amino acids) was shown to be toxic when expressed in BL21 (DE3) bacteria (FIG. 1).

Expression of Cel12A Variants

To overcome bacterial host death during expression of the Cel12A, variant proteins were designed. (See schematics of proteins presented in FIGS. 3A–3D.) A gene fragment encoding the catalytic domain (δCel12AH) downstream from the $[EP]_4$ linker was cloned under the control of T7/lac promoter in plasmid pET25b and expressed in *E. coli* BL21(DE3). The variant protein accumulated in cytoplasm of the host bacteria and no bacterial lysis was observed (FIG. 1). The growth rate of the bacteria was slightly inhibited due to the intensive production of the recombinant variant protein which accounted for about 40% of total protein content of the cells (FIG. 2). The variant protein, δCel12A, did not precipitate when incubated at 65° C. and retained activity on CMC as assessed by overlayer gel test.

A DNA fragment encoding a variant Cel12A that lacked the signal peptide (first 17 amino acids) was cloned into the pET25b plasmid and expressed in E. coli. Bacteria effectively produced active protein without cell lysis. However, the recombinant variant cellulase, Cel12A(sp-)H, was partially cleaved by bacterial protease and two bands were observed on SDS-polyacrylamide gels (FIG. 2), as well as on activity gels. Both variant cellulases were stable, and were stored at 4° C. for several weeks.

Characterization of Cel12A and Variants

The full-length cellulase expressed in E. coli has been characterized (Halldorsdottir, S. et al., Appl Microbiol Biotechnol, 49:277–284 (1998)). However, all activity tests described herein were conducted using full-length Cel12A and all variants. The full-length enzyme and all variants were tested with and without the His-tag (His6), and no differences in properties were observed. The effect of temperature on activity was investigated by incubating the proteins at temperatures ranging from 40° C. to 105° C. and then assaying for enzymatic activity. The activity of full-length Cel12A and Cel12A(sp-)H increased up to 105° C., while δCel12AH displayed maximal activity at about 90° C. (Table 1). The variant forms of the cellulase retained 95%–100% of their initial activity after 16 hours at 85° C. The half-life of activity at 90° C. for full-length Cel12A was 3 hours, for δCel12AH was 2 hours and for Cel12(sp-)H was 5 hours. The pH optima for the full-length enzyme and the variants were similar. All proteins were active over a broad pH range and expressed over 40% of maximal activity at pH ranging from about 4.0 to about 8.0 and over 20% of maximal activity at pH 10.

The variant Cel12A proteins had the same substrate specificities as full-length Cel12A protein and hydrolysed soluble polysaccharides with β1-4 and β1-3–β1-4 linkages. The variants proteins hydrolysed CMC, lichenian, glucomannan and had highest level of enzymatic activity when assayed using lichenian (7.2 U/mg). The cellulases had very low activity on Avicel and were not active on xylan and galactomannan. The variant cellulases had specific activities on CMC that were about 3 to about 4 times higher than the specific activity of the full-length protein (Table 1).

TABLE 1

| | Optimal temperature for catalysis (° C.) | Tm/Tm* (° C.) | specific activity on CMC (U/mg) | T½ at 90° C. (hours) |
|---|---|---|---|---|
| Cel12A | >105 | aggregates/120.0 | 0.7 | 3 |
| δCel12AH | 90 | 94.5/106.6 | 2.7 | 2 |
| Cel12A(sp-)H | >105 | 102.9/NE | 3.1 | 5 |
| Cel12A(sp-) | >105 | 103.2/120.0 | 3.1 | Retained 80% activity after 16 hours 45 minutes at 100° C. |

NE - not examined
Tm - unfolding temperature in 20 mM Tris-HCL pH 7.5
Tm* - unfolding temperature in 20 mM Tris-HCL pH 7.5/0.5% SDS

TABLE 2

| | Relative Catalytic Activity | |
|---|---|---|
| Sample | no SDS | with 0.5% SDS |
| Cel12A | 0.7 | 1 |
| δCel12AH | 1 | 0.86 |
| Cel12A(sp-)H | 1 | 0.94 |

DCS Studies

Intensive aggregation of the Cel12A (expressed as fluctuations of the Cp value), starting at temperatures of 65° C.–70° C. were observed in 20 mM Tris-HCl pH 7.5, and no thermal transition peaks could be detected. The variant δCel12A unfolded at 94.5° C. when studies under the same conditions (FIG. 5), and no aggregation was noted up to 105° C. The thermal denaturation of δCel12A was irreversible. Thermal transition of CelA(sp-)H occurred at 102.9° C. (FIG. 5), and thermal denaturation was irreversible. In contrast to xylanase, $Ca^{2+}$ had no stabilizing effect on the cellulases. However, the stability of the proteins was slightly enhanced by substrate (3° C. for δCel12AH).

All forms of the cellulase were stabilized by 0.5% (w/v) SDS. In addition, the detergent stabilized and prevented aggregation of full-length Cel12A (Cel12A underwent thermal transition at 120° C. in the presence of 0.5% SDS). Cel12A(sp-)H and δCel12AH unfolded at 120° C. and 106.5° C., respectively, in presence of SDS. The thermal transitions for all tested cellulases were fully reversible when SDS was present.

Tween 20 (polyoxyethylenesorbitan monolaurate) nonionic detergent did not stabilise the tested proteins at a concentration of 0.5%.

Discussion

The endo-glucanase Cel12A from R. marinus has been cloned and produced in E. coli (Halldorsdottir, S. et al., Appl Microbiol Biotechnol, 49:277–284 (1998)). Although the amount of protein produced in E. coli exceeded what could be obtained from R. marinas cultivations, the yield was comprehensively lower than expected. Particularly because expression was driven using a T7/lac promoter based system. Analysis of the primary structure of Cel12A revealed an explanation for the low production yield, and interesting organisational features of the enzyme. Notably, the N-terminal contains a hydrophobic region that has features which are characteristic of signal peptides. The results of the study described herein demonstrate that this putative signal peptide is responsible for the toxicity of full-length enzyme. The optical density drop that was observed in cultures of E. coli when trying to express the first 38 amino acid residues of the protein, was persistent several hours after induction suggesting that no post-induction cell division occurred.

Recombinant full-length Cel12A was not stable in solution or when heated to 65° C. In addition, the optimum growth temperature of R. marinus (65° C.) caused extensive aggregation at moderately high protein concentrations. No clear thermal transition of the full-length enzyme were observed on the calorimetric trace when the run was carried out without SDS, most likely because severe aggregation occurred before the protein was unfolded. Furthermore, a clearly visible aggregate was indeed observed when the sample was taken out of the DSC cell. However, a clear thermal transition (at 120° C.) with no aggregation was observed when full-length Cel12A was tested in the presence of 0.5% SDS. Interestingly, the specific activity of the full-length enzyme was higher in the presence of SDS. In contrast, the presence of SDS lead to a decrease in the specific activity of the variant lacking the first 17 amino acid residues (δCel12A) under the same conditions.

Cell associated glycosyl hydrolase activity has been reported earlier from *R. marinus* cultivations, where considerable activity was detected in the cell fraction (Dahlberg, L. et al., *Appl. Microbiol. Biotechnol.*, 40:63–68 (1993)). To determine if Cel12A is cell associated, *R. marinus* was cultivated in the presence of CMC and the endoglucanase activity was assayed. Activity was detected in the sonicated cell fraction and in the supernatant fraction, indicating that at least some Cel12A is membrane associated.

The variants of Cel12A described herein were readily produced in large quantities by expression in *E. coli* and had improved stability and activity relative to full length Cel12A. In addition the variant proteins (e.g., δCel12AH, Cel12A(sp-)H) did not deviate substantially from the full-length enzyme in their pH optima or substrate specificities. This is consistent with the fact that the integrity of the catalytic core was maintained, and the deletion of amino-terminal amino acids did not result in appreciable changes of the theoretically estimated isoelectric point of the enzyme. However, the deletion of the first 17 amino acid residues had a pronounced effect on the stability of the enzyme in aqueous media. As discussed earlier, the majority of the full-length enzyme after the first purification step was catalytically inactive, and heating the samples at 65° C. resulted in comprehensive loss of the enzyme due to aggregation. The hydrophobic residues of the putative signal peptide are likely to be solvent exposed and consequently would comprise the thermodynamic driving force for aggregation. Accordingly, heating the full-length protein can accelerate the aggregation process, since hydrophobic interactions increase with temperature in this region.

Glycosyl hydrolases are typically modular proteins, comprised of catalytic and auxiliary modules separated by recognisable linker sequences. Linker sequences occur in a variety of lengths and amino acid compositions depending on their origin (Tomme, P. et al., *Cellulose Hydrolysis by Bacteria and Fungi*. in: R. K. Poole, ed., *Advances in Microbial Physiology*, vol 37, London, Academic Press (1995)). Typically, linkers are rich in prolines, hydroxy amino acids, alanine or glycine, and the arrangement of these amino acids imparts flexibility necessary for their function. The putative signal peptide and the catalytic module of Cel12A are separated by a typical linker sequence. The four times repeat of glutamic acid and proline which preceding the catalytic core of the enzyme is reminiscent of the linkers that separate the different modules of the xylanase, Xyn10A from *R. marinus* (Nordberg, K. E. et al., *Biochimica et Biophysica Acta*, 1353:118–124 (1997)). In addition this structure (i.e., a linker sequence that links the putative signal peptide and the catalytic module) is shared with another family 12 glycosyl-hydrolase from the hyperthermophilic archaeon *Pyrococcus furiosus* (Bauer, M. W. et al., *J Bacteriology*, 181:284–290 (1999)).

The study described herein demonstrates that variant cellulases, that have the amino acid sequence of a thermostable cellulase wherein one or more amino acids which are not part of the catalytic domain of the enzyme are deleted, can be more easily produced and have improved stability and/or catalytic activity relative to certain full-length cellulases.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated nucleic acid molecule encoding a polypeptide having thermostable cellulase activity and having the amino acid sequence of SEQ ID NO:2, or encoding a truncated polypeptide such that one or more of the amino acid residues from position one to position 40 in SEQ ID NO: 2 are deleted, wherein said truncated polypeptide has a specific activity that is at least two times greater than the specific activity of the polypeptide having the full length sequence of SEQ ID NO:2, wherein the specific activity is assessed using carboxymethyl cellulose as substrate.

2. A nucleic acid construct comprising the nucleic acid molecule of claim 1 operably linked to a regulatory sequence.

3. A host cell comprising the nucleic acid construct of claim 2.

4. An isolated nucleic acid molecule having a nucleotide sequence selected from the group consisting of: nucleotides 52–783 of SEQ ID NO: 3, nucleotides 55–783 of SEQ ID NO: 3, nucleotides 58–783 of SEQ ID NO: 3, nucleotides 61–783 of SEQ ID NO: 3, nucleotides 64–783 of SEQ ID NO: 3, nucleotides 67–783 of SEQ ID NO: 3, nucleotides 70–783 of SEQ ID NO: 3, nucleotides 73–783 of SEQ ID NO: 3, nucleotides 76–783 of SEQ ID NO: 3, nucleotides 79–783 of SEQ ID NO: 3, and nucleotides 82–783 of SEQ ID NO: 3, wherein said nucleic acid sequence encodes a thermostable cellulase polypeptide having a specific activity that is at least two times greater than the specific activity of the polypeptide having the full-length sequence of SEQ ID NO: 2, where the specific activity is assessed using carboxymethyl cellulose as substrate.

5. A nucleic acid construct comprising the nucleic acid of claim 4 operably linked to a regulatory sequence.

6. A recombinant host cell comprising the nucleic acid construct of claim 5.

7. The isolated nucleic acid molecule of claim 4 wherein the nucleic acid has the sequence of nucleotides 52–783 of SEQ ID NO: 3.

8. An isolated nucleic acid molecule having a nucleotide sequence selected from the group consisting of: nucleotides 85–783 of SEQ ID NO: 3, nucleotides 88–783 of SEQ ID NO: 3, nucleotides 91–783 of SEQ m 3, nucleotides 94–783 of SEQ ID NO: 3, nucleotides 97–783 of SEQ ID NO:3, nucleotides 100–783 of SEQ ID NO:3, nucleotides 103–783 of SEQ ID NO:3, nucleotides: 106–783 of SEQ ID NO:3, nucleotides 109–783 of SEQ ID NO:3 and nucleotides 112–783 of SEQ ID NO; 3, wherein said nucleic acid sequence encodes a thermostable cellulase polypeptide having a specific activity that is at least two times greater than the specific activity of the polypeptide having the full-length sequence of SEQ ID NO:2, where the specific activity is assessed using carboxymethyl cellulose as substrate.

9. A nucleic acid construct comprising the nucleic acid molecule of claim 8 operably linked to a regulatory sequence.

10. A recombinant host cell comprising the nucleic acid construct of claim 9.

11. The isolated nucleic acid molecule of claim 8 wherein the nucleic acid sequence comprises the sequence of nucleotides 112–783 of SEQ ID NO: 3.

12. An isolated nucleic acid molecule encoding a fusion protein comprising a thermostable cellulase polypeptide having the amino acid sequence of SEQ ID NO:2 and a fusion partner or a fusion protein comprising a thermostable cellulase variant of a glycosyl hydrolase of family 12 and a fusion partner, wherein said variant is truncated such that one or more of the amino acid residues in position one to position 40 in SEQ ID NO: 2 are deleted, wherein said variant polypeptide has a specific activity that is at least two times greater than the specific activity of the polypeptide having the full length sequence of SEQ ID NO:2, wherein the specific activity is assessed using carboxymethyl cellulose as substrate.

13. A nucleic acid construct comprising the nucleic acid molecule of claim 12 operably linked to a regulatory sequence.

14. A recombinant host cell comprising the nucleic acid construct of claim 13.

15. A method for producing a thermostable cellulase comprising maintaining the host cell of claim 14 under conditions suitable for expression of said nucleic acid construct, whereby said thermostable cellulase is produced.

16. A method for producing a thermostable cellulase comprising maintaining the host cell of claim 10 under conditions suitable for expression of said nucleic acid construct, whereby said thermostable cellulase is produced.

17. A method for producing a thermostable cellulase comprising maintaining the host cell of claim 6 under conditions suitable for expression of said construct, whereby said thermostable cellulase is produced.

18. The method of claim 17 further comprising recovering said thermostable cellulase.

\* \* \* \* \*